United States Patent [19]
Tang et al.

[11] Patent Number: 5,821,226
[45] Date of Patent: Oct. 13, 1998

[54] BAL C-TAIL DRUG DELIVERY MOLECULES

[75] Inventors: Jordan J. N. Tang, Edmond; Chi-Sun Wang, Oklahoma City, both of Okla.

[73] Assignee: Oklahoma Medical Research Foundation, Oklahoma City, Okla.

[21] Appl. No.: 482,262

[22] Filed: Jun. 7, 1995

Related U.S. Application Data

[63] Continuation-in-part of Ser. No. 347,718, Dec. 1, 1994, Pat. No. 5,696,087.

[51] Int. Cl.⁶ .......................... A61K 38/16; A61K 38/08; A61K 38/10

[52] U.S. Cl. ................................ 514/12; 514/13; 514/14; 514/15; 514/16; 514/17; 514/18

[58] Field of Search ............................. 514/12, 13, 14, 514/15, 16, 17, 18

[56] References Cited

U.S. PATENT DOCUMENTS

| | | | |
|---|---|---|---|
| Re. 33,885 | 4/1992 | Mattson | 514/53 |
| 4,602,003 | 7/1986 | Malinow | 514/26 |
| 4,944,944 | 7/1990 | Tang et al. | 424/94.6 |
| 4,976,968 | 12/1990 | Steiner | 424/491 |
| 5,017,565 | 5/1991 | Lange, III et al. | 514/54 |
| 5,063,210 | 11/1991 | Lange, III et al. | 514/54 |
| 5,173,408 | 12/1992 | Lange, III et al. | 435/69.1 |
| 5,200,183 | 4/1993 | Tang et al. | 424/94.6 |
| 5,376,640 | 12/1994 | Miyazaki et al. | 514/12 |
| 5,519,001 | 5/1996 | Kushwaha et al. | 514/12 |

FOREIGN PATENT DOCUMENTS

| | | |
|---|---|---|
| 0 075 444 A2 | 9/1982 | European Pat. Off. . |
| 0 075 444 B1 | 9/1982 | European Pat. Off. . |
| 0075444 A | 9/1982 | European Pat. Off. . |
| 0 333 523 | 9/1989 | European Pat. Off. . |
| WO 89/08465 | 9/1989 | WIPO . |
| WO 91/06286 | 5/1991 | WIPO . |
| WO 91/06287 | 5/1991 | WIPO . |
| WO 91/15234 | 10/1991 | WIPO . |
| WO 94/20610 | 7/1994 | WIPO . |
| WO 96/17054 | 6/1996 | WIPO . |

OTHER PUBLICATIONS

Baba, T, et al., "Structure of Human Milk Bile Salt Activated Lipase," *Biochemistry*, 30:500–510 (1991).

Barr, et al., "Protocol for Efficient Secretion of HSA Developed from Pichia pastoris," *Pharmaceutical Engineering* 12:48–51 (1992).

Bevington, P.R., *"Propagation of Errors," Data Reduction and Error Analysis for the Physical Sciences* 56–65 and 204–246, McGraw–Hill, New York (1969).

Bierman, E.L., "Disorders of the Vascular System: Atherosclerosis and Other Forms of Arteriosclerosis," in *Harrison's Principles of Internal Medicine* 1014–1024, (E. Braunwald et al. 1987).

Bitter, G.A. et al., "Expression and Secretion Vectors for Yeast," *Methods in Enzymology* (Wu and Grossman, eds.) 153:516–544 (1987).

Bosner, et al., "Assessment of percent cholesterol absorption in humans with stable isotypes," *J. of Lipid Res.* 34:1047 (1993).

Bosner, et al., "Receptor–like function of heparin in the binding and update of neutal lipids," *Proc. Natl. Acad. Sci. USA* 85:7438–7442 (1988).

Bremel, R.D., Yom, H.C. and Bleck, G.T., "Alteration of Milk Composition UsingMolecular Genetics," *J. Dairy Sci.* 72:2826–2833 (1989).

Brodt–Eppley and Hui, "Dietary regulation of cholesterol esterase mRNA level in rat pancreas," *J. of Lipid Res.* 35:27 (1994).

Brown, M.S., and J.L. Goldstein, "The Hyperlipoproteinemias and Other Disorders of Lipid Metabolism," in *Harrison's Principles of Internal Medicine* 1650–1661.

Clare, J.J. et al., "High–Level Expression of Tetanus Toxin Fragment in *Pichia Pastoris* Strains Containing Multiple Tanden Integrations of the Gene," *Bio/Technology* 9:455–460 (1991).

Clark, et al., "Inhibition of Hypercholesterolemia (Hyper C) By Specific Pancreatic Cholesterol Ester Hydrolase (PCEH) Inhibitors," *FASEB J.* 6"PA1388 (1992).

Cullen, D. et al., "Controlled Expression and Secretion of Bovine Chymosin in *Aspergillus Nidulans*," *Bio/Technology* 5:369–378 (1987).

Cullen, D., Gray, G.L., and Berka, R.M., "Molecular Cloning Vectors for Aspergillus and Neurospora," n *A Survey of Molecular Cloning Vectors and their Uses*, (Butterworth Publishers, Stoneham, MA (1986)*.

DiPersio, et al., "Purification of Pancreatic Cholesterol Esterase Expressed in Recombinant Baculovirus–Infected Sf9 Cells," *Protein Expr. Purif.* 3:114–120 (1992).

Downs, D. et al., "Proline–rich domain and glycosylation are not essential for the enzymic activity of bile salt–activated lipase. Kinae studies of a truncated form of the enzyme (T–BAL) expressed in *E. coli,*" *Biochemistry* 33:7980–7985 (1994).

Dubois, et al., "Colorimetric Method for Determination of Sugars and Related Substances," *Anal. Chem.* 28:350–356 (1956).

(List continued on next page.)

*Primary Examiner*—Herbert J. Lilling
*Attorney, Agent, or Firm*—Arnall Golden & Gregory, LLP

[57] ABSTRACT

Drug delivery conjugates of including a BAL C-tail peptide including all or a portion of the carboxy terminal region of human bile salt-activated lipase (BAL) conjugated to a biologically active substance are described. The C-tail peptide-drug conjugates, when orally ingested, compete with native BAL in binding to the intestinal surface, and, as a result, permit drug compositions to be delivered specifically to the intestine. Useful C-tail peptides are derivatives of the carboxy terminal region of BAL derived from all or portion of the region containing amino acid residues 539 to 722, and have a mucin-like structure containing at least three of the repeating proline-rich units of eleven amino acid residues each.

29 Claims, 1 Drawing Sheet

OTHER PUBLICATIONS

Elhammer, A.P. et al., "The Specificity of UDP–GalNAc: Polypeptide N–Acetylgalactosaminyltransferase as Inferred from a Database of in Vivo Substrates and from the in Vitro Glycosylation of Proteins and Peptides," *J.Biol.Chem.* 268:10029–10038 (1993).

Freed, et al., "Bile salt–stimulated lipase in non–primate milk: longitudinal variation and lipase characteristics in cat and dog milk," *Biochim. and Biophy. Acta* 878:209–215 (1986).

Gallo, et al., "Inhibition of Cholesterol Absorption in Rat Intestine with a Specific Cholesterol Esterase Inhibitor," *FASEB Journal* 6(4): PA1388 (1992).

Ganong, W.F., *Review of Medical Physiology* 249–250 (Lange Medical Publications, 1985)*.

Gray, et al., "Primary structure of *Mucor miehei* aspartyl protease: evidence for a zymogen intermediate," *Gene* 48:41–53 (1987).

Griggs, et al., "Identification and Quantitation of Alditol Acetates of Neutral and Amino Sugars from Mucins by Automated Gas–Lipid Chromatography," *Anal. Biochem.* 43:369–381 (1971).

Hall and Muller, "Studies on the Bile Salt Stimulated Lipolytic Activity of Human Milk Using Whole Milk as Source of Both Substrate and Enzyme," *Pediatr. Res.* 16:251–255 (1982).

Hernell and Blackberg, "Bile–Salt–Stimulated Lipase of Human Milk and Lipid Digestion in the Neonatal Period," *J. Pediatr. Gastro. and Nutri.* 2(Suppl. 1):S242–S247 (1983).

Hewick, R.M., et al., "A Gas–Lipid Solid Phase Peptide and Protein Sequenator," *J. Biol. Chem.* 256:7990–7997 (1981).

Huang and Hui, "Metabolic fate of pancrease–derived cholesterol esterase in intestine: an in vitro study using Caco–2 cells," *J. of Lipid Res.* 31:2029 (1990).

Hui, D.Y., and J.A. Kissel, "Sequence identify between human pancreatic cholesterol esterase and bile salt–stimulated milk lipase," *FEBS Lett.* 276:131–134 (1990).

Innis, M.A., and D.H. Gelfand, "Optimization of PCRs," *PCR Protocols. A Guide to Methods and Application* 3–12, Innis, M.A., et al. (Eds.), Academic Press, New York, N.Y. (1990).

Jaenisch, R., "Transgenic Animals," *Science* 240:1468–1474 (1988).

Klag, M.J., et al., "Serum Cholesterol in Young Men and Subsequent Cardiovascular Disease," *New Eng. J. Med.*, 328(5), pp.313–318 (Feb. 4, 1993).

Kraft, et al., "Using Mini–Prep Plasmid DNA for Sequencing Double Stranded Templates with Sequenase," *BioTechniques* 6:544–547 (1988).

Leary, W.E., "Survey Finds Major Gains in Cutting Blood Cholesterol," *New York Times*, section A, p. 18, col. 3, (Jun. 16, 1993).

Lopez–Candales, et al., "Cholesterol Transport Function of Pancreatic Cholesterol Esterase: Directed Sterol Uptake and Esterification in Enterocytes," *Biochem.* 32:12085–12089 (1993).

Lowry, O.H., et al., "Protein Measurement with the Folin Phenol Reagent," *J. Biol. Chem.* 193:265 (1951).

Luckow, V.A. and Summers, M.D., "Trends in the Development of Baculovirus Expression Vectors", *Bio/Technology* 6:47 (1988).

McKean, et al., "Effects of Inhibitors of Pancreatic Cholesterol Ester Hydrolase (PCEH) On $^{14}$C–cholesterol Absorption in Animal Models," *FASEB Journal* 6(4):PA1388 (1992).

Nilsson, J., et al., "cDNA cloning of human–milk bile–salt–stimulated lipase and evidence for its identiy to pancreatic carboxylic ester hydrolase," *Eur. J. Biochem.* 192:543–550 (1990).

Nilsson–Ehle, P., and M.C. Schotz, "A stable, radioactive substrate emulsion for assay of lipoprotein lipase," *J. Lipid Res.* 17:536–541 (1976).

Poorman, et al., "Isolated and Characterization of Native Human Renin Derived from Chinese Hamster Ovary Cells," *Proteins* 1:139–145 (1986).

Reue, K., et al., "cDNA cloning of carboxyl ester lipase from human pancrease reveals a unique proline–rich repeat unit," *J. Lipid Res.* 32:267–276 (1991).

Rudd, Edwin A., "Pancreatic carboxyl ester," *Lipases* (Elsevier, publishers, 1984).

Scahill, S.J., et al., "Expression and characterization of the product of a human immune interferon cDNA gene in Chinese hamster ovary cells," *Proc. Natl. Acad. Sci., U.S.A* 80:4654–4658 (1983).

Segel, I.H., "Enzyme Activation," *Enzyme Kinetics* 227–231, John Wiley & Sons, New York (1975).

Studier, F.W., et al., "Use of T7 RNA Polymerase to Direct Expression of Cloned Genes," *Methods Enzymol.* 185:60–89 (1990).

Wang, et al., "Kinetics of Acylglycerol Sequential Hydrolysis by Human Milk Bile Salt Activated Lipase and Effect of Taurocholate as Fatty Acid Acceptor," *Biochem.* 27:4834 (1988).

Wang & Kloer, "Kinetic Properties of Human Pancreatic Carboxylesterase," *Biochim. et Biophys. Acta* 754:142–149 (1983).

Wang, C.–S., and J.A. Hartsuck, "Bile salt–activated lipase. A multiple function lipolytic enzyme," *Biochim. Biophys. Acta* 1166:1–19 (1993).

Wang and Johnson, "Purification of Human Milk Bile Salt–Activated Lipase," *Anal. Biochem.* 133:457–461 (1983).

Wang, C.–S., "Human Milk Bile Salt–activated Lipase," *J. Biol. Chem.* 256:10198–10202 (1981).

Wang, "Acyl–chain specificity of human milk bile–salt–activated lipase," *Biochem. J.* 279:297–302 (1991).

Wang, C.–S., and R.L. Smith, "Lowry Determination of Protein in the Presence of Triton X–100," *Anal. Biochem.* 63:414–417 (1975).

Wang, et al., "Bile Salt–Activated Lipase Mediates Cholesterol Absorption by Binding of its Mucin–Like Region to Intestinal Surface," *Science* (1995)*.

Wang, et al., "Bile–salt–activated lipase: effect on kitten growth rate," *Am. J. Clin. Nutr.* 49:457–463 (1989).

Wang, "Purification of Carboxyl Ester Lipase from Human Pancrease and the Amino Acid Sequence of the N–Terminal Region," *Biochem. and Biophys. Res. Comm.* 155:950 (1988).

Westphal, H., "Transgenic Mammals and biotechnology," *FASEB J.* 3:117–120 (1989).

"CV Therapeutics Begins Phase I Trial on Cholesterol–Reduction Agent," *Biotech. Bulletin* p. 11 (1994).

Creighton, *Proteins: Structure and Molecular Properties*, 79–86 (W.H. Freeman & Co., San Francisco, 1983)*.

FIG. 1

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 722 amino acids
        ( B ) TYPE: amino acid
        ( D ) TOPOLOGY: linear     ( i i ) MOLECULE TYPE: protein     ( i i i ) HYPOTHETICAL: NO     ( v ) FRAGMENT TYPE: internal     ( x i ) SEQUENCE DESCRIPTION: SEQ ID NO:1:

```
Ala Lys Leu Gly Ala Val Tyr Thr Glu Gly Gly Phe Val Glu Gly Val
 1               5                  10                  15
Asn Lys Lys Leu Gly Leu Leu Gly Asp Ser Val Asp Ile Phe Lys Gly
                20                  25                  30
Ile Pro Phe Ala Ala Pro Thr Lys Ala Leu Glu Asn Pro Gln Pro His
            35                  40                  45
Pro Gly Trp Gln Gly Thr Leu Lys Ala Lys Asn Phe Lys Lys Arg Cys
        50                  55                  60
Leu Gln Ala Thr Ile Thr Gln Asp Ser Thr Tyr Gly Asp Glu Asp Cys
65                  70                  75                  80
Leu Tyr Leu Asn Ile Trp Val Pro Gln Gly Arg Lys Gln Val Ser Arg
                85                  90                  95
Asp Leu Pro Val Met Ile Trp Ile Tyr Gly Gly Ala Phe Leu Met Gly
                100                 105                 110
Ser Gly His Gly Ala Asn Phe Leu Asn Asn Tyr Leu Tyr Asp Gly Glu
            115                 120                 125
Glu Ile Ala Thr Arg Gly Asn Val Ile Val Val Thr Phe Asn Tyr Arg
        130                 135                 140
Val Gly Pro Leu Gly Phe Leu Ser Thr Gly Asp Ala Asn Leu Pro Gly
145                 150                 155                 160
Asn Tyr Gly Leu Arg Asp Gln His Met Ala Ile Ala Trp Val Lys Arg
                165                 170                 175
Asn Ile Ala Ala Phe Gly Gly Asp Pro Asn Asn Ile Thr Leu Phe Gly
                180                 185                 190
Glu Ser Ala Gly Gly Ala Ser Val Ser Leu Gln Thr Leu Ser Pro Tyr
            195                 200                 205
Asn Lys Gly Leu Ile Arg Arg Ala Ile Ser Gln Ser Gly Val Ala Leu
        210                 215                 220
Ser Pro Trp Val Ile Gln Lys Asn Pro Leu Phe Trp Ala Lys Lys Val
225                 230                 235                 240
Ala Glu Lys Val Gly Cys Pro Val Gly Asp Ala Ala Arg Met Ala Gln
                245                 250                 255
Cys Leu Lys Val Thr Asp Pro Arg Ala Leu Thr Leu Ala Tyr Lys Val
                260                 265                 270
Pro Leu Ala Gly Leu Glu Tyr Pro Met Leu His Tyr Val Gly Phe Val
            275                 280                 285
Pro Val Ile Asp Gly Asp Phe Ile Pro Ala Asp Pro Ile Asn Leu Tyr
        290                 295                 300
```

```
Ala  Asn  Ala  Ala  Asp  Ile  Asp  Tyr  Ile  Ala  Gly  Thr  Asn  Asn  Met  Asp
305                 310                 315                           320

Gly  His  Ile  Phe  Ala  Ser  Ile  Asp  Met  Pro  Ala  Ile  Asn  Lys  Gly  Asn
                    325                 330                      335

Lys  Lys  Val  Thr  Glu  Glu  Asp  Phe  Tyr  Lys  Leu  Val  Ser  Glu  Phe  Thr
               340                 345                           350

Ile  Thr  Lys  Gly  Leu  Arg  Gly  Ala  Lys  Thr  Thr  Phe  Asp  Val  Tyr  Thr
          355                      360                      365

Glu  Ser  Trp  Ala  Gln  Asp  Pro  Ser  Gln  Glu  Asn  Lys  Lys  Lys  Thr  Val
     370                      375                 380

Val  Asp  Phe  Glu  Thr  Asp  Val  Leu  Phe  Leu  Val  Pro  Thr  Glu  Ile  Ala
385                      390                 395                           400

Leu  Ala  Gln  His  Arg  Ala  Asn  Ala  Lys  Ser  Ala  Lys  Thr  Tyr  Ala  Tyr
                    405                      410                      415

Leu  Phe  Ser  His  Pro  Ser  Arg  Met  Pro  Val  Tyr  Pro  Lys  Trp  Val  Gly
               420                      425                 430

Ala  Asp  His  Ala  Asp  Asp  Ile  Gln  Tyr  Val  Phe  Gly  Lys  Pro  Phe  Ala
          435                      440                 445

Thr  Pro  Thr  Gly  Tyr  Arg  Pro  Gln  Asp  Arg  Thr  Val  Ser  Lys  Ala  Met
     450                      455                 460

Ile  Ala  Tyr  Trp  Thr  Asn  Phe  Ala  Lys  Thr  Gly  Asp  Pro  Asn  Met  Gly
465                      470                 475                           480

Asp  Ser  Ala  Val  Pro  Thr  His  Trp  Glu  Pro  Tyr  Thr  Thr  Glu  Asn  Ser
               485                      490                           495

Gly  Tyr  Leu  Glu  Ile  Thr  Lys  Lys  Met  Gly  Ser  Ser  Ser  Met  Lys  Arg
               500                 505                           510

Ser  Leu  Arg  Thr  Asn  Phe  Leu  Arg  Tyr  Trp  Thr  Leu  Thr  Tyr  Leu  Ala
          515                 520                      525

Leu  Pro  Thr  Val  Thr  Asp  Gln  Glu  Ala  Thr  Pro  Val  Pro  Pro  Thr  Gly
     530                 535                      540

Asp  Ser  Glu  Ala  Thr  Pro  Val  Pro  Pro  Thr  Gly  Asp  Ser  Glu  Thr  Ala
545                      550                      555                      560

Pro  Val  Pro  Pro  Thr  Gly  Asp  Ser  Gly  Ala  Pro  Pro  Val  Pro  Pro  Thr
                    565                      570                      575

Gly  Asp  Ser  Gly  Ala  Pro  Pro  Val  Pro  Pro  Thr  Gly  Asp  Ser  Gly  Ala
               580                      585                      590

Pro  Pro  Val  Pro  Pro  Thr  Gly  Asp  Ser  Gly  Ala  Pro  Pro  Val  Pro  Pro
          595                      600                      605

Thr  Gly  Asp  Ser  Gly  Ala  Pro  Pro  Val  Pro  Pro  Thr  Gly  Asp  Ser  Gly
     610                      615                      620

Ala  Pro  Pro  Val  Pro  Pro  Thr  Gly  Asp  Ser  Gly  Ala  Pro  Pro  Val  Pro
625                      630                      635                      640

Pro  Thr  Gly  Asp  Ala  Gly  Pro  Pro  Val  Pro  Pro  Thr  Gly  Asp  Ser
                    645                      650                      655

Gly  Ala  Pro  Pro  Val  Pro  Pro  Thr  Gly  Asp  Ser  Gly  Ala  Pro  Pro  Val
               660                      665                      670

Thr  Pro  Thr  Gly  Asp  Ser  Glu  Thr  Ala  Pro  Val  Pro  Pro  Thr  Gly  Asp
          675                      680                      685

Ser  Gly  Ala  Pro  Pro  Val  Pro  Pro  Thr  Gly  Asp  Ser  Glu  Ala  Ala  Pro
          690                      695                      700

Val  Pro  Pro  Thr  Asp  Asp  Ser  Lys  Glu  Ala  Gln  Met  Pro  Ala  Val  Ile
705                      710                      715                      720

Arg  Phe
```

( 2 ) INFORMATION FOR SEQ ID NO:2:

( i ) SEQUENCE CHARACTERISTICS:
        ( A ) LENGTH: 742 amino acids
        ( B ) TYPE: amino acid
        ( D ) TOPOLOGY: linear     ( i i ) MOLECULE TYPE: protein     ( i i i ) HYPOTHETICAL: NO     ( v ) FRAGMENT TYPE: internal     ( i x ) FEATURE:
        ( A ) NAME/KEY: Modified-site
        ( B ) LOCATION: 186..187
        ( D ) OTHER INFORMATION: /note= "Position 187 represents a
            potential N- linked glycosylation site."

( i x ) FEATURE:
        ( A ) NAME/KEY: Modified-site
        ( B ) LOCATION: 193..194
        ( D ) OTHER INFORMATION: /note= "The serine at position 194
            represents an active site serine."

( i x ) FEATURE:
        ( A ) NAME/KEY: misc. feature
        ( B ) LOCATION: 1..742
        ( D ) OTHER INFORMATION: /Function = "Amino acid sequence for
            the Human Milk Bile Salt-activated Lipase."

( x i ) SEQUENCE DESCRIPTION: SEQ ID NO:2:

```
Met Gly Arg Leu Gln Leu Val Val Leu Gly Leu Thr Cys Cys Trp Ala
 1               5                  10                  15

Val Ala Ser Ala Ala Lys Leu Gly Ala Val Tyr Thr Glu Gly Gly Phe
            20                  25                  30

Val Glu Gly Val Asn Lys Lys Leu Gly Leu Leu Gly Asp Ser Val Asp
         35                  40                  45

Ile Phe Lys Gly Ile Pro Phe Ala Ala Pro Thr Lys Ala Leu Glu Asn
     50                  55                  60

Pro Gln Pro His Pro Gly Trp Gln Gly Thr Leu Lys Ala Lys Asn Phe
 65                  70                  75                  80

Lys Lys Arg Cys Leu Gln Ala Thr Ile Thr Gln Asp Ser Thr Tyr Gly
                 85                  90                  95

Asp Glu Asp Cys Leu Tyr Leu Asn Ile Trp Val Pro Gln Gly Arg Lys
            100                 105                 110

Gln Val Ser Arg Asp Leu Pro Val Met Ile Trp Ile Tyr Gly Gly Ala
        115                 120                 125

Phe Leu Met Gly Ser Gly His Gly Ala Asn Phe Leu Asn Asn Tyr Leu
    130                 135                 140

Tyr Asp Gly Glu Glu Ile Ala Thr Arg Gly Asn Val Ile Val Val Thr
145                 150                 155                 160

Phe Asn Tyr Arg Val Gly Pro Leu Gly Phe Leu Ser Thr Gly Asp Ala
                165                 170                 175

Asn Leu Pro Gly Asn Tyr Gly Leu Arg Asp Gln His Met Ala Ile Ala
            180                 185                 190

Trp Val Lys Arg Asn Ile Ala Ala Phe Gly Gly Asp Pro Asn Asn Ile
        195                 200                 205

Thr Leu Phe Gly Glu Ser Ala Gly Gly Ala Ser Val Ser Leu Gln Thr
    210                 215                 220

Leu Ser Pro Tyr Asn Lys Gly Leu Ile Arg Arg Ala Ile Ser Gln Ser
225                 230                 235                 240

Gly Val Ala Leu Ser Pro Trp Val Ile Gln Lys Asn Pro Leu Phe Trp
```

-continued

```
                          245                       250                       255
     Ala  Lys  Lys  Val  Ala  Glu  Lys  Val  Gly  Cys  Pro  Val  Gly  Asp  Ala  Ala
                    260                      265                      270

Arg  Met  Ala  Gln  Cys  Leu  Lys  Val  Thr  Asp  Pro  Arg  Ala  Leu  Thr  Leu
                    275                      280                      285

Ala  Tyr  Lys  Val  Pro  Leu  Ala  Gly  Leu  Glu  Tyr  Pro  Met  Leu  His  Tyr
                    290                      295                      300

Val  Gly  Phe  Val  Pro  Val  Ile  Asp  Gly  Asp  Phe  Ile  Pro  Ala  Asp  Pro
     305                      310                      315                      320

Ile  Asn  Leu  Tyr  Ala  Asn  Ala  Ala  Asp  Ile  Asp  Tyr  Ile  Ala  Gly  Thr
                              325                      330                      335

Asn  Asn  Met  Asp  Gly  His  Ile  Phe  Ala  Ser  Ile  Asp  Met  Pro  Ala  Ile
                    340                      345                      350

Asn  Lys  Gly  Asn  Lys  Val  Thr  Glu  Glu  Asp  Phe  Tyr  Lys  Leu  Val
                    355                      360                      365

Ser  Glu  Phe  Thr  Ile  Thr  Lys  Gly  Leu  Arg  Gly  Ala  Lys  Thr  Thr  Phe
                    370                      375                      380

Asp  Val  Tyr  Thr  Glu  Ser  Trp  Ala  Gln  Asp  Pro  Ser  Gln  Glu  Asn  Lys
     385                      390                      395                      400

Lys  Lys  Thr  Val  Val  Asp  Phe  Glu  Thr  Asp  Val  Leu  Phe  Leu  Val  Pro
                              405                      410                      415

Thr  Glu  Ile  Ala  Leu  Ala  Gln  His  Arg  Ala  Asn  Ala  Lys  Ser  Ala  Lys
                              420                      425                      430

Thr  Tyr  Ala  Tyr  Leu  Phe  Ser  His  Pro  Ser  Arg  Met  Pro  Val  Tyr  Pro
                              435                      440                      445

Lys  Trp  Val  Gly  Ala  Asp  His  Ala  Asp  Asp  Ile  Gln  Tyr  Val  Phe  Gly
                    450                      455                      460

Lys  Pro  Phe  Ala  Thr  Pro  Thr  Gly  Tyr  Arg  Pro  Gln  Asp  Arg  Thr  Val
     465                      470                      475                      480

Ser  Lys  Ala  Met  Ile  Ala  Tyr  Trp  Thr  Asn  Phe  Ala  Lys  Thr  Gly  Asp
                              485                      490                      495

Pro  Asn  Met  Gly  Asp  Ser  Ala  Val  Pro  Thr  His  Trp  Glu  Pro  Tyr  Thr
                    500                      505                      510

Thr  Glu  Asn  Ser  Gly  Tyr  Leu  Glu  Ile  Thr  Lys  Lys  Met  Gly  Ser  Ser
                    515                      520                      525

Ser  Met  Lys  Arg  Ser  Leu  Arg  Thr  Asn  Phe  Leu  Arg  Tyr  Trp  Thr  Leu
          530                      535                      540

Thr  Tyr  Leu  Ala  Leu  Pro  Thr  Val  Thr  Asp  Gln  Glu  Ala  Thr  Pro  Val
     545                      550                      555                      560

Pro  Pro  Thr  Gly  Asp  Ser  Glu  Ala  Thr  Pro  Val  Pro  Pro  Thr  Gly  Asp
                              565                      570                      575

Ser  Glu  Thr  Ala  Pro  Val  Pro  Pro  Thr  Gly  Asp  Ser  Gly  Ala  Pro  Pro
                    580                      585                      590

Val  Pro  Pro  Thr  Gly  Asp  Ser  Gly  Ala  Pro  Pro  Val  Pro  Pro  Thr  Gly
                    595                      600                      605

Asp  Ser  Gly  Ala  Pro  Pro  Val  Pro  Pro  Thr  Gly  Asp  Ser  Gly  Ala  Pro
                    610                      615                      620

Pro  Val  Pro  Pro  Thr  Gly  Asp  Ser  Gly  Ala  Pro  Pro  Val  Pro  Pro  Thr
     625                      630                      635                      640

Gly  Asp  Ser  Gly  Ala  Pro  Pro  Val  Pro  Pro  Thr  Gly  Asp  Ser  Gly  Ala
                              645                      650                      655

Pro  Pro  Val  Pro  Pro  Thr  Gly  Asp  Ala  Gly  Pro  Pro  Val  Pro  Pro
                    660                      665                      670
```

|   |   |   |   |   |   |   |   |   |   |   |   |   |   |   |
|---|---|---|---|---|---|---|---|---|---|---|---|---|---|---|
| Thr | Gly | Asp | Ser | Gly | Ala | Pro | Pro | Val | Pro | Pro | Thr | Gly | Asp | Ser | Gly |
|   | 675 |   |   |   |   | 680 |   |   |   |   | 685 |

Ala Pro Pro Val Thr Pro Thr Gly Asp Ser Glu Thr Ala Pro Val Pro
    690             695                 700

Pro Thr Gly Asp Ser Gly Ala Pro Pro Val Pro Thr Gly Asp Ser
705             710                 715                 720

Glu Ala Ala Pro Val Pro Pro Thr Asp Asp Ser Lys Glu Ala Gln Met
            725             730                 735

Pro Ala Val Ile Arg Phe
            740

(2) INFORMATION FOR SEQ ID NO:3:

(i) SEQUENCE CHARACTERISTICS:
        (A) LENGTH: 3018 base pairs
        (B) TYPE: nucleic acid
        (C) STRANDEDNESS: single
        (D) TOPOLOGY: linear     (ii) MOLECULE TYPE: cDNA     (iii) HYPOTHETICAL: NO     (iv) ANTI-SENSE: NO     (ix) FEATURE:
        (A) NAME/KEY: misc. feature
        (B) LOCATION: 1..742
        (D) OTHER INFORMATION: /Function = "Nucleotides 679 through
        2904 encode the amino acid sequence for the Human Milk
        Bile Salt- activated Lipase."

(xi) SEQUENCE DESCRIPTION: SEQ ID NO:3:

```
CTCAATTGGA  GGATCAAAGT  TGAGAAAAGT  AATATTCGAC  ATTTTTCGAT  TCAACGGAGT     60
GGCCACCAAG  ACGATGTCAT  AGAAGTCTGA  ACGAGTCTCA  GTTCCAATTT  GGTAGACCAC    120
TTCATACATC  TTTGTTGGAT  TTCCTGTGTA  CTTGGTCTTT  GTTTTCTCCT  CGATGTACAT    180
TACTGAGCCA  GATATAAGAT  TGCTTTTGGA  TGCCTGCAGA  AGCCCTGAGC  AAACAAGTTT    240
ATTGCCACCT  TCTACTGCCC  AAAGGCCAGA  ATCAGAACAG  GACAGTGACA  CCGCCCCCAC    300
AAAGGCATTG  ATGTCCGTGC  TTTGGCCATA  ATTGACCCTC  ATAACAGGAG  CAATCATTTC    360
ATTGAGGAAC  TTCTCAGAAA  AGCCGGCCTT  TTGCAAGGTT  TCAAGAAGTG  TTCGATTAAG    420
CATTCCAAGG  AAGTCATCTC  CTCCTAGAGC  ATGAAGTAAT  TTTTCGACAC  TACTGAAGGC    480
ATAGTCATGA  GACTGGTAGC  GGTAGATCCT  CATGAACTTG  TCTAACACGT  CCTCTACCCA    540
CATGTGCATA  CGGAGGGATT  GAAATCCATA  GCGCCAAACT  AATTTAATCA  CGTTAATTAT    600
GAACCAGTTG  CTCTCCTCAA  ATACCAGAGT  CTCTCCATTA  TATATCCCCA  GTAGGCCACC    660
CAGAGGCTGA  TGCTCACCAT  GGGGCGCCTG  CAACTGGTTG  TGTTGGGCCT  CACCTGCTGC    720
TGGGCAGTGG  CGAGTGCCGC  GAAGCTGGGC  GCCGTGTACA  CAGAAGGTGG  GTTCGTGGAA    780
GGCGTCAATA  AGAAGCTCGG  CCTCCTGGGT  GACTCTGTGG  ACATCTTCAA  GGGCATCCCC    840
TTCGCAGCTC  CCACCAAGGC  CCTGGAAAAT  CCTCAGCCAC  ATCCTGGCTG  GCAAGGGACC    900
CTGAAGGCCA  AGAACTTCAA  GAAGAGATGC  CTGCAGGCCA  CCATCACCCA  GGACAGCACC    960
TACGGGGATG  AAGACTGCCT  GTACCTCAAC  ATTTGGGTGC  CCCAGGGCAG  GAAGCAAGTC   1020
TCCCGGGACC  TGCCCGTTAT  GATCTGGATC  TATGGAGGCG  CCTTCCTCAT  GGGGTCCGGC   1080
CATGGGGCCA  ACTTCCTCAA  CAACTACCTG  TATGACGGCG  AGGAGATCGC  CACACGCGGA   1140
AACGTCATCG  TGGTCACCTT  CAACTACCGT  GTCGGCCCCC  TTGGGTTCCT  CAGCACTGGG   1200
GACGCCAATC  TGCCAGGTAA  CTATGGTCTT  CGGGATCAGC  ACATGGCCAT  TGCTTGGGTG   1260
```

-continued

| | | | | | | |
|---|---|---|---|---|---|---|
| AAGAGGAATA | TCGCGGCCTT | CGGGGGGGAC | CCCAACAACA | TCACGCTCTT | CGGGGAGTCT | 1320 |
| GCTGGAGGTG | CCAGCGTCTC | TCTGCAGACC | CTCTCCCCCT | ACAACAAGGG | CCTCATCCGG | 1380 |
| CGAGCCATCA | GCCAGAGCGG | CGTGGCCCTG | AGTCCTGGG | TCATCCAGAA | AAACCCACTC | 1440 |
| TTCTGGGCCA | AAAAGGTGGC | TGAGAAGGTG | GGTTGCCCTG | TGGGTGATGC | CGCCAGGATG | 1500 |
| GCCCAGTGTC | TGAAGGTTAC | TGATCCCCGA | GCCCTGACGC | TGGCCTATAA | GGTGCCGCTG | 1560 |
| GCAGGCCTGG | AGTACCCCAT | GCTGCACTAT | GTGGGCTTCG | TCCCTGTCAT | TGATGGAGAC | 1620 |
| TTCATCCCCG | CTGACCCGAT | CAACCTGTAC | GCCAACGCCG | CCGACATCGA | CTATATAGCA | 1680 |
| GGCACCAACA | ACATGGACGG | CCACATCTTC | GCCAGCATCG | ACATGCCTGC | CATCAACAAG | 1740 |
| GGCAACAAGA | AACTCACGGA | GGAGGACTTC | TACAAGCTGG | TCAGTGAGTT | CACAATCACC | 1800 |
| AAGGGGCTCA | GAGGCGCCAA | GACGACCTTT | GATGTCTACA | CCGAGTCCTG | GGCCCAGGAC | 1860 |
| CCATCCCAGG | AGAATAAGAA | GAAGACTGTG | GTGGACTTTG | AGACCGATGT | CCTCTTCCTG | 1920 |
| GTGCCCACCG | AGATTGCCCT | AGCCCAGCAC | AGAGCCAATG | CCAAGAGTGC | CAAGACCTAC | 1980 |
| GCCTACCTGT | TTTCCCATCC | CTCTCGGATG | CCCGTCTACC | CCAAATGGGT | GGGGGCCGAC | 2040 |
| CATGCAGATG | ACATTCAGTA | CGTTTTCGGG | AAGCCCTTCG | CCACCCCCAC | GGGCTACCGG | 2100 |
| CCCCAAGACA | GGACAGTCTC | TAAGGCCATG | ATCGCCTACT | GGACCAACTT | TGCCAAAACA | 2160 |
| GGGGACCCCA | ACATGGGCGA | CTCGGCTGTG | CCCACACACT | GGGAACCCTA | CACTACGGAA | 2220 |
| AACAGCGGCT | ACCTGGAGAT | CACCAAGAAG | ATGGGCAGCA | GCTCCATGAA | GCGGAGCCTG | 2280 |
| AGAACCAACT | TCCTGCGCTA | CTGGACCCTC | ACCTATCTGG | CGCTGCCCAC | AGTGACCGAC | 2340 |
| CAGGAGGCCA | CCCCTGTGCC | CCCCACAGGG | GACTCCGAGG | CCACTCCCGT | GCCCCCCACG | 2400 |
| GGTGACTCCG | AGACCGCCCC | CGTGCCGCCC | ACGGGTGACT | CCGGGGCCCC | CCCCGTGCCG | 2460 |
| CCCACGGGTG | ACTCCGGGGC | CCCCCCCGTG | CCGCCCACGG | GTGACTCCGG | GGCCCCCCCC | 2520 |
| GTGCCGCCCA | CGGGTGACTC | CGGGGCCCCC | CCCGTGCCGC | CCACGGGTGA | CTCCGGGGCC | 2580 |
| CCCCCGTGC | CGCCCACGGG | TGACTCCGGG | GCCCCCCCG | TGCCGCCCAC | GGGTGACTCC | 2640 |
| GGCGCCCCCC | CCGTGCCGCC | CACGGGTGAC | GCCGGGCCCC | CCCCGTGCC | GCCCACGGGT | 2700 |
| GACTCCGGCG | CCCCCCCCGT | GCCGCCCACG | GGTGACTCCG | GGGCCCCCCC | CGTGACCCCC | 2760 |
| ACGGGTGACT | CCGAGACCGC | CCCCGTGCCG | CCCACGGGTG | ACTCCGGGGC | CCCCCCTGTG | 2820 |
| CCCCCCACGG | GTGACTCTGA | GGCTGCCCCT | GTGCCCCCCA | CAGATGACTC | CAAGGAAGCT | 2880 |
| CAGATGCCTG | CAGTCATTAG | GTTTTAGCGT | CCCATGAGCC | TTGGTATCAA | GAGGCCACAA | 2940 |
| GAGTGGGACC | CCAGGGGCTC | CCCTCCCATC | TTGAGCTCTT | CCTGAATAAA | GCCTCATACC | 3000 |
| CCTGAAAAAA | AAAAAAAA | | | | | 3018 |

BAL C-TAIL DRUG DELIVERY MOLECULES

This application is a continuation in part of U.S. Ser. No. 08/347,718, filed Dec. 1, 1994, now U.S. Pat. No. 5,696,087 which is incorporated herein by reference.

The U.S. government has certain rights in this invention by virtue of research grant HD-23472 from the National Institutes of Health.

BACKGROUND OF THE INVENTION

The present invention is in the field of drug delivery and more particularly relates to the use of bile salt-activated lipase fragments to deliver drugs in the intestine.

Drug delivery takes a variety of forms, depending on the agent to be delivered and the administration route. A preferred mode of administration is non-invasive; i.e., administration via oral passages. Some compounds are not suited for such administration, however, since they are degraded by conditions in the gastrointestinal tract or do not penetrate well into the blood stream.

Controlled release systems for drug delivery are often designed to administer drugs in specific areas of the body. In the gastrointestinal tract it is critical that the drug not be entrained beyond the desired site of action and eliminated before it has had a chance to exert a topical effect or to pass into the bloodstream. If a drug delivery system can be made to adhere to the lining of the appropriate viscus, its contents will be delivered to the targeted tissue as a function of proximity and duration of the contact.

The digestive process involves the physical and chemical breakdown of ingested food, followed by selective absorption of digested molecules in the intestine. Protease, lipases and other hydrolases secreted into the intestine effect the chemical breakdown of proteins, carbohydrates and other larger molecules present in food. Since food is a complex chemical mixture, ingested food often contains an imbalance of nutrients, harmful substances, and molecular forms that cannot be digested or absorbed. In some cases, it would be desirable to supplement the digestive enzymes in the intestine with additional enzymes to provide new digestive capabilities, or to provide binding molecules or other compounds that could eliminate undesirable food molecules or prevent their absorption.

At present, digestive supplementation is neither sophisticated nor widely utilized. The most widely practiced digestive supplementations involve dietary supplements aimed at balancing and supplementing nutrient content of food, and the use of digestive supplements for breakdown of lactose. The breakdown of lactose is particularly important due to the prominence of dairy products in human diet and the widespread prevalence of lactose intolerance in human populations. Humans cannot absorb lactose, which is a prominent sugar in milk. Many human populations lack the enzyme lactase which breaks down lactose into glucose and galactose, two sugars which are readily absorbed by the intestine. In the absence of lactase, lactose accumulates in the lumen of the small intestine. The large osmotic effect of unabsorbed lactose leads to an influx of fluid into the intestine causing the uncomfortable symptoms of lactose intolerance.

One problem with current digestive supplements is the transient nature of their effect. Ingested food and supplements, following the natural course of the digestive process, pass quickly through the intestinal tract. Accordingly, there is a need for a method of providing digestive supplements and other therapeutic compounds in the intestine over an extended period of time.

It is therefore an object of the present invention to provide compositions and methods for delivering therapeutic compounds to the intestinal lining.

SUMMARY OF THE INVENTION

Compositions derived from all or a portion of the carboxy terminal region (C-tail) of human bile salt-activated lipase (BAL) coupled to a therapeutic compound are described, which, when orally ingested, bind to the intestinal surface, thus delivering the therapeutic compound to the intestinal surface. Targeting the therapeutic compound to the intestinal surface can increase the uptake of the compound, alter the therapeutic efficacy of the compound or be used to act in conduction with the BAL receptor to alter uptake of cholesterol and lipids. The latter can be particularly advantageous in terms of compositions for weight control, and well as in the treatment of atherosclerosis. Useful derivatives of the carboxy terminal region of BAL are derived from all or portion of the region containing amino acid residues 539 to 722, and have a mucin-like structure containing at least three of the repeating proline-rich units of eleven amino acid residues each. Preferred proline-rich units have the consensus sequence PVPPTGDSGAP (Sequence ID No. 2).

The BAL C-tail is attached a substance to be delivered, using standard technology, either directly to the compound or to a pharmaceutical carrier for the compound. Examples of useful carriers include microspheres. Examples of useful therapeutics in addition to dietary aids include vaccines for oral administration. The C-tail fragments offers a significant advance in the art of the pharmaceutical delivery devices, in that they specifically deliver the bioactive composition to the intestine where it exerts a therapeutic effect. The C-tails can also be used to screen for compounds that affect binding of BAL to the receptor.

DETAILED DESCRIPTION OF THE INVENTION

Compositions including all or a portion of the carboxy terminal (C tail) region of bile salt-activated lipase (BAL), or functional equivalents thereof, (C-tail peptides) are described, which, in the intestine, compete with native BAL in binding to the intestinal surface, and which are conjugated to a biologically active composition. The BAL C-tail molecules are attached to a substance to be delivered thus enabling the substance to be delivered specifically to the intestine upon oral administration of the conjugate. In the intestine, these compositions bind to the intestinal surface resulting in delivery and/or long-term presence of the therapeutic compound at the intestinal lining.

Bile Salt-activated Lipase

Warm-blooded animals synthesize many forms of lipases of different structures and activities, which are secreted by mammary gland cells and by cells in several of the digestive organs, including the pancreas, stomach, and small intestine. Bile salt-activated lipase (BAL), which is virtually inactive by itself toward physiological substrates, is activated in the intestine by bile salts. BALs are synthesized and secreted by the pancreas and also by the mammary glands of only few species, including humans, gorillas, cats, and dogs. The amino acid and cDNA sequences of human milk BAL are the same as those of pancreatic BAL, also known as pancreatic carboxylesterase, and closely related to or the same as lipases referred to in the literature as lysophospholipase, cholesterol esterase, sterol ester hydrolase, non-specific lipase, lipase A, carboxyl ester lipase, and cholesterol ester hydrolase, with certain species differences, primarily with respect to the number of repeating units in the carboxy region (Wang and Hartsuck, *Biochim. Biophys. Acta* 1166:1–19 (1993)). Pancreatic BAL is distinct from other types of non-bile salt activated lipases, such as pancreatic lipase and phospholipase.

In the intestinal lumen, BAL becomes attached to the intestinal surfaces, most likely the surface of intestinal epithelial lining cells via a specific receptor. It can be released from the lumenal surface by EGTA, galactose and fucose, but not by heparin, isotonic buffer, or sodium chloride, as demonstrated below. BAL, in the required presence of bile salts, is essential for hydrolyzing cholesterol esters to free cholesterol or to bind free cholesterol in the food. Both of these processes are necessary to allow the uptake of cholesterol since it is the only known pancreatic lipolytic enzyme that can mediate cholesterol uptake. BAL also hydrolyses carboxyl ester bonds of acylglycerols, phospholipid, and vitamin esters, forming fatty acids and glycerol, and can act on emulsified, micellar, or soluble substrates. It is thought that bile salt causes conformational change in BAL to provide active site access for the bulky substrate molecule and provides additional lipid binding capability in forming the enzyme-substrate complex. Additionally, it is thought that bile salt acts as a fatty acid acceptor during BAL catalysis.

Figure 1:
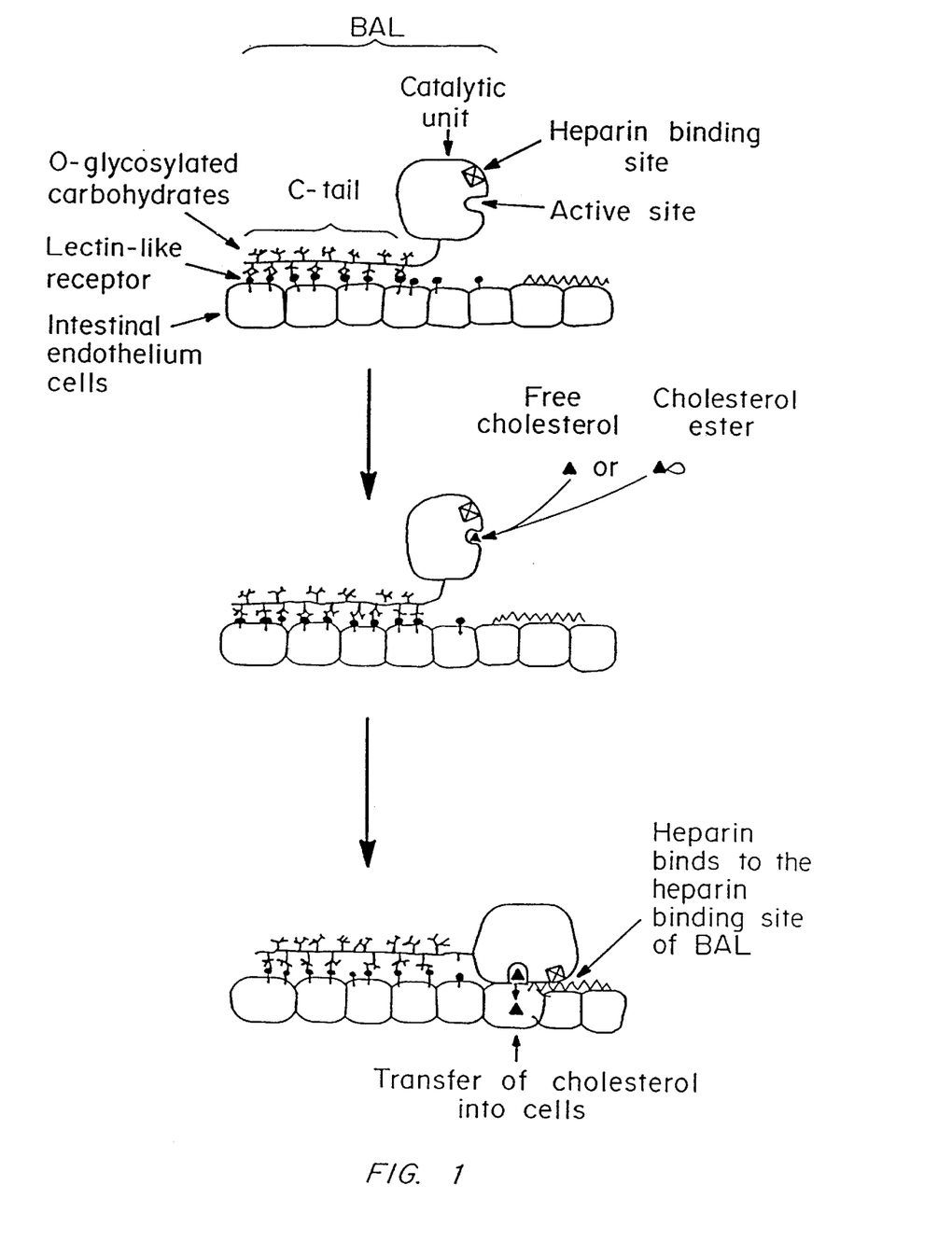
FIG. 1 shows the proposed binding of BAL to intestinal endothelium cells via the C-tail O-glycosylated carbohydrate binding to a lectin-like receptor, binding of cholesterol and cholesterol ester to BAL, hydrolyzing cholesterol ester by BAL, followed by transfer of enzyme bound cholesterol into cells.

The proposed mechanism for the action of BAL is shown in FIG. 1. BAL binds via the C-tail O-glycosylated carbohydrates to a lectin-like receptor on the surface of intestinal endothelium cells. The catalytic unit of the enzyme remains away from the endothelium cells, with the heparin binding site and active site exposed. Free cholesterol or cholesterol ester is then bound to the active site, and, in the case of cholesterol ester, it is hydrolyzed to free cholesterol. The catalytic unit then binds to the heparin on the cell surface and transfers the cholesterol into the cells.

Cholesterol, fatty acids, and monoacyglycerols derived from lipolysis by BAL in the intestinal lumen are taken up by the intestinal epithelial lining cell (mucosal cell), where these are reesterified to intracellular triacylglycerols. Cholesterol interacts in the cell with these reesterified triacylglycerols plus apolipoproteins and phospholipid to form chylomicrons and very low density lipoproteins, which are secreted into the lymphatics that ultimately join the blood vascular system for systemic circulation.

The Carboxy Terminal Region of the BAL Molecule

The full, mature, human BAL contains 722 amino acid residues (Sequence ID No. 1). The carboxy terminal region of BAL refers to a region in the native BAL molecule including residues 539 to 722. This carboxy terminal region of BAL, along with derivatives of this region that retain the intestinal binding activity, are referred to herein as "C-tail." The C-tail of the human BAL molecule has many O-linked oligosaccharide units which form a mucin-like structure. The amino acid sequence of the native human C-tail contains sixteen repeating proline-rich units of eleven amino acid residues each, most having the consensus sequence of PVPPTGDSGAP (Sequence ID No. 2) (Baba et al., *Biochemistry* 30:500–510 (1991)). By performing the beta-elimination reaction, the native C-tail was determined to be O-glycosylated primarily at threonine and, to a small degree, if any, at one serine residue. It is believed that the serine residue, which has an adjacent aspartic acid, is not favorable for the O-glycosylation (Elhammer et al., *J. Biol. Chem.* 268:10029–10038 (1993)). A peptide prepared by cyanogen bromide digestion of the C-tail was found to contain most of the carbohydrate of the native BAL (Baba et al. (1991)).

As described below, truncated versions of BAL which include the C-tail alone can bind to the intestinal surface, and in fact, can compete with native BAL for this binding, and can serve to deliver drugs attached to the C-tail directly to the intestinal surface.

C-tail proteins

C-tail proteins, methods and for manufacture, and use for inhibition of cholesterol uptake, are described in detail in "Methods and Compositions for Reducing Cholesterol Absorption", U.S. Ser. No. 08/479,160, filed Jun. 7, 1995 and in U.S. Ser. No. 08/347,718 filed Dec. 1, 1994, the teachings of which are incorporated herein.

Derivatives of the carboxy terminal region of BAL, derived from all or portion of the region containing amino acid residues 539 to 722, and having a mucin-like structure containing at least three of the repeating proline-rich units of eleven amino acid residues each, is referred to herein as C-tail. C-tail protein as used herein includes both the protein and the protein in combination with attached saccharide units. As used herein, a proline-rich unit refers to any of the repeated eleven amino acid groups present in any naturally occurring form of BAL, or derivatives thereof which, when combined with two or more other proline-rich units, results in a protein which binds to intestinal endothelium cells and/or inhibits the binding of native BAL. Preferred proline-rich units have the consensus sequence PVPPTGDSGAP (amino acids 581 to 591 of Sequence ID No. 2). As used herein, a "C-tail protein" refers to any protein containing three or more proline-rich units as defined above, which binds to intestinal endothelium cells and/or inhibits the binding of native BAL. This can be achieved, for example, through the use of BAL consisting of all or part of the mucin-like C-tail region of native BAL. Native BAL is a form of C-tail protein.

A C-tail protein should include at least three of the repeating proline-rich units of eleven amino acid residues each. The rat pancreatic esterase C-tail which has only four repeating units still binds to rat intestine surface. Preferred C-tail proteins have at least 10, and most preferably at least 16, proline-rich units. It is expected that C-tail proteins with fewer proline-rich units will bind to intestinal surface with a lower affinity. The binding affinity of any C-tail protein can be increased by using proline-rich units that most closely match the consensus sequence (Sequence ID No. 2). C-tail proteins can be constructed by combining three or more proline-rich units, where the proline-rich units have the native amino acid sequence of a proline-rich unit from any BAL, have the consensus amino acid sequence of the human proline-rich unit, or derivatives of these amino acid sequences, such that the C-tail protein retains the ability to bind to intestinal endothelium cells and/or inhibit the binding of native BAL.

Amino acid sequence variants

The C-tail protein may be O-glycosylated to different extents with respect to the number of threonine and serine residues, and can include amino acid deletions, substitutions, or additions which do not significantly impair binding to the intestinal surface. The substitutions, deletions, or additions to C-tail proteins, which do not alter binding are readily determined by a screening assay, in which the protein is allowed to bind to intestinal surface, then removed by washing with buffer with increasing concentrations of salt. An example of a BAL which contains a deletion not affecting binding of the C-tail is a BAL lacking the heparin binding site, which is postulated to be present between amino acid residues 56 and 62 (Baba et al. (1991)).

Amino acid sequence variants of C-tail protein fall into one or more of three classes: substitutional, insertional or deletional variants. Insertions include amino and/or carboxyl terminal fusions as well as intrasequence insertions of single or multiple amino acid residues. Fusions include hybrids of mature BAL and the C-tail protein with polypeptides that are homologous with BAL, for example, in the case of human BAL, secretory leaders from other secreted human proteins. Fusions also include hybrids of BAL and the C-tail protein with polypeptides homologous to the host cell but not to BAL, as well as, polypeptides heterologous to both the host cell and BAL. Preferred fusions are amino terminal fusions with either prokaryotic peptides or signal peptides of prokaryotic, yeast, viral or host cell signal sequences. It is not essential that the signal sequence be devoid of any residual mature sequence from the protein whose secretion it ordinarily directs but this is preferable in order to avoid the secretion of a C-tail protein fusion.

Insertions can also be introduced within the coding sequence of the proline-rich unit repeat region of the C-tail protein. Such insertions can include the addition of unrelated amino acids or the insertion of one or more additional proline-rich units. In the context of inserted amino acids, "unrelated" amino acids refer to amino acid sequences that are unrelated to the sequence of the proline-rich units of BAL. In the case of proline-rich units, the inserted units can be heterologous units from non-human BAL, units having the consensus sequence, or additional repeats of individual human proline-rich units. In the case of insertion of unrelated amino acids, however, the insertion will ordinarily consist of smaller insertions than those of amino or carboxyl terminal fusions, or than those of proline-rich units, on the order of 1 to 4 residues.

Insertional amino acid sequence variants of C-tail proteins are those in which one or more amino acid residues are introduced into a predetermined site in the target C-tail protein. Most commonly, insertional variants are fusions of heterologous proteins or polypeptides to the amino or carboxyl terminus of the C-tail protein. Preferably, these heterologous polypeptides are heterologous forms of the proline-rich units present in human BAL. Immunogenic C-tail protein derivatives are made by fusing a polypeptide sufficiently large to confer immunogenicity to the target sequence by cross-linking in vitro or by recombinant cell culture transformed with DNA encoding the fusion. Such immunogenic polypeptides can be bacterial polypeptides such as trpLE, beta-galactosidase and the like.

Deletions are characterized by the removal of one or more amino acid residues from the C-tail protein sequence. It is preferred that deletions involve deletions of entire proline-rich units. If individual amino acids within the proline-rich units are deleted, no more than about from 2 to 6 residues are deleted at any one site within the C-tail protein molecule.

These variants ordinarily are prepared by site specific mutagenesis of nucleotides in the DNA encoding the C-tail protein, thereby producing DNA encoding the variant, and thereafter expressing the DNA in recombinant cell culture. However, variant C-tail protein fragments having up to about 100 to 150 residues may be conveniently prepared by in vitro synthesis. The variants typically exhibit the same qualitative biological activity as the naturally-occurring analogue, that is, specific intestinal binding, although variants also are selected in order to modify the characteristics of the C-tail protein as will be more fully described below.

While the site for introducing an amino acid sequence variation is predetermined, the mutation per se need not be predetermined. For example, in order to optimize the performance of a mutation at a given site, random mutagenesis may be conducted at the target codon or region and the expressed C-tail protein variants screened for the optimal combination of desired properties. Techniques for making substitution mutations at predetermined sites in DNA having a known sequence are well known, for example M13 primer mutagenesis.

Amino acid substitutions are typically of single residues; insertions usually will be on the order of about from 1 to 10 amino acid residues, or entire proline-rich units; and deletions will range about from 1 to 30 residues, or entire proline-rich units. Deletions or insertions preferably are made in adjacent pairs, that is a deletion of 2 residues or insertion of 2 residues. Substitutions, deletions, insertions or any combination thereof may be combined to arrive at a final construct. Obviously, the mutations that will be made in the DNA encoding the variant BAL or C-tail protein must not place the sequence out of reading frame and preferably will not create complementary regions that could produce secondary mRNA structure (EP 75,444A).

Substitutional variants are those in which at least one residue in the C-tail protein has been removed and a different residue inserted in its place. Such substitutions generally are made in accordance with the following Table I when it is desired to finely modulate the characteristics of C-tail protein or BAL.

TABLE I

| Original Residue | Exemplary Substitutions |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table I, that is, selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in BAL or C-tail protein properties will be those in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue;

(c) a residue having an electropositive side chain, for example, lysyl, arginyl, or histidyl, is substituted for (or by) an electronegative residue, for example, glutamyl or aspartyl; or (d) a residue having a bulky side chain, for example, phenylalanine, is substituted for (or by) one not having a side chain, for example, glycine.

Substitutional or deletional mutagenesis can be employed to eliminate N- or O-linked glycosylation sites (for example by deletion or substitution of asparaginyl residues in Asn-X-Thr glycosylation sites), improve expression of BAL or C-tail protein or alter the half life of the protein. Alternatively, unglycosylated BAL or C-tail protein can be produced in recombinant prokaryotic cell culture. Such unglycosylated forms are expected to lack, or have reduced, intestinal binding activity. Deletions of cysteine or other labile residues also may be desirable, for example in increasing the oxidative stability or selecting the preferred disulfide bond arrangement of BAL. Deletions or substitutions of potential proteolysis sites, for example, Arg, is accomplished for example by deleting one of the basic residues or substituting one by glutaminyl or histidyl residues.

Full length BAL which has an inactivated catalytic site can also be used for competitive inhibition of binding of cholesterol. Since the catalytic site is inactivated, the BAL cannot facilitate uptake of cholesterol. The catalytic site can be inactivated by amino acid deletion or substitution in the active site of the recombinant BAL. The catalytic site can also be inactivated by chemical modification of BAL at or near the active site, for example, by proteolysis or other enzymic reactions, by binding of an irreversible enzyme inhibitor to the catalytic site, or by means which disrupt the three dimensional conformation of the catalytic unit of BAL (since the binding of the C-tail to intestine is not dependent on its conformation). Examples of disruptive means include detergents and heat.

Useful BAL derivatives that do not hydrolyze cholesterol esters or bind heparin include polypeptides that may or may not be substantially homologous with BAL. These BAL derivatives are produced by the recombinant or organic synthetic preparation of BAL fragments or by introducing amino acid sequence variations into intact BAL so that it no longer demonstrates cholesterol ester hydrolysis and/or heparin binding activity as defined above.

BAL derivatives that do not hydrolyze cholesterol esters or bind heparin as described above are useful as immunogens for raising antibodies to active BAL. Such BAL derivatives, referred to as "BAL protein antagonists" may be used to neutralize the cholesterol uptake-mediating activity or BAL. Such a BAL protein antagonist may bind to the intestinal lining thereby blocking binding of native BAL. BAL protein antagonists are useful in the therapy of various cholesterol disorders for example, hypercholesterolemia, especially hypercholesterolemia exacerbated by dietary cholesterol intake.

BAL, BAL derivatives, and C-tail protein molecules may also be covalently modified. Such modifications are made by reacting targeted amino acid residues of the recovered or synthesized protein with an organic derivatizing agent that is capable of reacting with selected side chains or terminal residues. Alternately, post-translational modification in selected recombinant host cells may be used to modify the protein. The resulting covalent derivatives are useful as immunogens or to identify residues important for biological activity as well as for altering pharmacological characteristics of the molecule, such as half life, binding affinity and the like, as would be known to the ordinarily skilled artisan.

Certain post-translational derivatizations are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be used.

Other post-translational modifications include hydroxylation of proline and lysine, phosphorylation of hydroxyl groups of seryl or threonyl residues, methylation of the o-amino groups of lysine, arginine, and histidine side chains (Creighton, *Proteins: Structure and Molecular Properties* pages 79–86 (W. H. Freeman & Co., San Francisco, 1983)), acetylation of the N-terminal amine and, in some instances, amidation of the C-terminal carboxyl.

Sugars

Sugar or sugar analogue containing compounds can also be synthesized by chemical reactions to mimic the C-tail structures. As defined herein, C-tail includes C tail as well as molecules which mimic C tail. Sugar or sugar analogs can be used to bind the intestinal surface and compete with endogenous BAL in the same manner as the C-tail itself. Galactose and fucose can elute endogenous bound BAL from rat intestinal surface, indicating that synthetic mimics of C-tail containing these sugars or their structural analogues can be used to affect the binding to intestinal surface. Since the C-tail contains repeating sequences and many glycosylation sites, the synthetic mimics can contain many sugar containing sites. The chemical linkages of sugars can be modeled based on the oligosaccharide structures of the C-tail, or the structural analogues of these oligosaccharide structures may contain essential features for effective binding to the intestinal BAL receptors. The sugars can be chemically attached to a polymer to create repeating units. Examples of suitable polymers include polypeptides, polyethylene glycol, dextran like sugar polymers and other synthetic polymers with appropriate functional groups for chemical linkage to sugars.

Coupling

Any of a variety of bioactive agents may be attached to the C-tail to permit delivery of the bioactive molecule to the intestine. For example, the C tails can be modified by covalent attachment of a bioactive agent to a carboxylic group or amino group on the C tail. The C tails can be modified using any of a number of different coupling chemistries that covalently attach ligands to C tails.

One useful protocol involves the "activation" of hydroxyl groups on the C tail carbonyldiimidazole (CDI) in aprotic solvents such as DMSO, acetone, or THF. CDI forms an imidazolyl carbamate complex with the hydroxyl group which may be displaced by binding the free amino group of a bioactive ligand such as a protein. The reaction is an N-nucleophilic substitution and results in a stable N-alkylcarbamate linkage of the ligand to the C tail. The resulting ligand-C tail complex is stable and resists hydrolysis for extended periods of time.

Another coupling method involves the use of 1-ethyl-3-(3-dimethylaminopropyl) carbodiimide (EDAC) or "water-soluble CDI" in conjunction with N-hydroxylsulfosuccinimide (sulfo NHS) to couple the exposed carboxylic groups of the C tail to the free amino groups of bioactive ligands. EDAC and sulfo-NHS form an activated ester with the carboxylic acid groups of the C tail which react with the amine end of a ligand to form a C tail bond. The resulting peptide bond is resistant to hydrolysis. The use of sulfo-NHS in the reaction increases the efficiency of the EDAC coupling by a factor of ten-fold and provides for exceptionally gentle conditions that ensure the viability of the ligand-C tail complex. These protocols permit the activation of either hydroxyl or carboxyl groups on the C tail, and attachment of the desired bioactive ligand.

A useful coupling procedure for attaching ligands with free hydroxyl and carboxyl groups to the C tail involves the use of the cross-linking agent, divinylsulfone. This method is useful for attaching sugars or other hydroxylic compounds to hydroxyl groups on the C tail. The activation involves the reaction of divinylsulfone with the hydroxyl groups of the C tail to a vinylsulfonyl ethyl ether. The vinyl groups will couple to alcohols, phenols and amines. Activation and coupling take place at pH 11. The linkage is stable in the pH range from 1–8 and is suitable for transit through the intestine. Any suitable coupling method known to those skilled in the art may be used to couple bioactive ligands to the C tail.

The therapeutic compound can be covalently coupled to C-tail protein either directly or indirectly using a linker molecule. Linker molecules will typically be used when additional flexibility or space is needed between the C-tail protein and the therapeutic compound. Any suitable molecule that can be coupled to both C-tail protein and a therapeutic compound can be used as a linked. Exemplary linkers are peptides or molecules with straight carbon chains. Because the C-tail composition will be used in the intestine, the bond or linker coupling the C-tail protein and the therapeutic compound must be stable in the intestinal environment.

Bioactive Agents

Any kind of bioactive agent can be attached to the C-tail using standard techniques. The resulting conjugate of the C-tail and the bioactive agent is referred to herein as a C-tail composition or a C-tail-drug conjugate. The C-tail fragments may be attached to any biologically active agent. The term biologically active material refers to a protein, carbohydrate, nucleic acid, lipid, organic compound such as a drug, or a combinations thereof, that causes a biological effect when administered in vivo to an animal including humans.

Nonlimiting examples are antigens, enzymes, hormones, receptors, peptides, proteins, polysaccharides, nucleic acids, nucleosides, nucleotides, liposomes, vitamins, minerals, inorganic compounds and viruses. The C-tail also can be used to deliver procaryotic and eucaryotic cells, e.g., bacteria, yeast, and mammalian cells, including human cells, and components thereof, such as cell walls, and conjugates of cellular components.

Examples of useful proteins include hormones such as insulin, growth hormones including somatometins, transforming growth factors, and other growth factors, antigens for oral vaccines, enzymes such as lactase or lipases, and digestive aids such as pancreatin.

Examples of useful drugs include ulcer treatments such as Carafate™ from Marion Pharmaceuticals, neurotransmitters such as L-DOPA, antihypertensives or saluretics such as Metolazone from Searle Pharmaceuticals, carbonic anhydrase inhibitors such as Acetazolamide from Lederle Pharmaceuticals, insulin like drugs such as glyburide, a blood glucose lowering drug of the sulfonylurea class, synthetic hormones such as Android F from Brown Pharmaceuticals and Testred (methyltestosterone) from ICN Pharmaceuticals, and antiparasitics such as mebendzole (Vermox™, Jannsen Pharmaceutical).

The C-tail drug conjugates are especially useful for treatment of inflammatory bowel diseases such as ulcerative colitis and Crohn's disease. In ulcerative colitis, inflammation is restricted to the colon, whereas in Crohn's disease, inflammatory lesions may be found throughout the gastrointestinal tract, from the mouth to the rectum. Sulfasalazine is one of the drugs that is used for treatment of the above diseases. Sulfasalazine is cleaved by bacteria within the colon to sulfapyridine, an antibiotic, and to 5-amino salicylic acid, an anti-inflammatory agent. The 5-amino salicylic acid is the active drug and it is needed locally. Direct administration of the degradation product (5-amino salicylic acid) may be more beneficial. A protein-drug delivery system could improve the therapy by retaining the drug for a prolonged time in the intestinal tract. For Crohn's disease, retention of 5-aminosalicylic acid in the upper intestine is of great importance, since bacteria cleave the sulfasalazin in the colon, the only way to treat inflammations in the upper intestine is by local administration of 5-aminosalicylic acid.

Antigens can be attached to the peptide to provide a vaccine. The vaccines can be produced to have different retention times in the gastrointestinal tract depending on the strength of the covalent bond binding the peptide to the vaccine. The different retention times, among other factors, can stimulate production of more than one type (IgG, IgM, IgA, IgE, etc.) of antibody. The term antigen includes any chemical structure that stimulates the formation of antibody or elicits a cell-mediated response, including but not limited to protein, polysaccharide, nucleoprotein, lipoprotein, synthetic polypeptide, or a small molecule linked to a protein. Specific antigens that can be attached to the peptide include attenuated or killed viruses, toxoids, polysaccharides, cell wall and surface or coat proteins of viruses and bacteria. These can also be used in combination with conjugates, adjuvants, or other antigens. For example, Hemophilus influenzae in the form of purified capsular polysaccharide (Hib) can be used alone or as conjugate with diphtheria toxoid. Examples of organisms from which these antigens are derived include poliovirus, rotavirus, hepatitis A, B, and C, influenza, rabies, HIV, measles, mumps, rubella, *Bordetella pertussus, Streptococcus pneumoniae,* Diphtheria, Tetanus, Cholera, Salmonella, Neisseria, Shigella, and Enterotoxigenic *E. coli.*

C tail can also be used to deliver water soluble or water insoluble drugs such as nonsteroidal anti-inflammatory compounds, anesthetics, chemotherapeutic agents, immunosuppressive agents, steroids, antibiotics, antivirals, antifungals, steroidal antiinflammatories, and anticoagulants.

Imaging agents also may be attached to C-tail, including metals, radioactive isotopes, radioopaque agents, fluorescent dyes, and radiolucent agents. Radioisotopes and radioopaque agents include gallium, technetium, indium, strontium, iodine, barium, and phosphorus.

The therapeutic compound (i.e., the biologically active agent) attached to C-tail can be any compound that will have a useful effect when delivered to the intestinal lining. The therapeutic compound can act to either reduce or enhance the uptake of a compound ingested by the individual, or to break down harmful compounds. For example, the therapuetic compound can be an enzyme, non-enzymatic binding molecule, or a ligand. An enzyme that catabolizes an undesirable compound ingested by the individual, or an antibody or receptor specific for such a compound, would be useful a the therapeutic compound. Because the C-tail composition will be used in the intestine the therapeutic compound must be stable an active in the intestinal environment.

Preferred therapeutic compounds are catabolic enzymes, catalyzing the breakdown of specific molecules, especially enzymes with activities not normally present in the intestines. A preferred therapeutic compound of this type is lactase. A C-tail/lactase composition can be used to deliver lactase to the intestinal lining of individuals who lack lactase or have a diminished lactase activity. C-tail/lactase will bind to the intestinal lining and maintain lactase activity over an extended period, breaking down ingested lactose and thereby alleviating the symptoms of lactose intolerance.

Oral Administration

In the preferred embodiment, the C-tail-drug conjugate is administered orally in an amount effective for a particular therapeutic application. The dosage will vary depending on the formulation, the rate of excretion, individual variations such as the number of receptors on the intestinal surface, the type of therapy, and the frequency of administration, as well as other factors routinely optimized by physicians. In one embodiment, the BAL C-tail composition is administered orally in an amount effective to reduce or enhance uptake of certain compounds from food, or lower the intestinal concentration of an undesirable compound.

Pharmaceutical compositions containing the C-tail-bioactive agent conjugate, designed to improve the pharmaceutical activity of the C-tail protein-drug conjugate when administered to a patient in a therapeutically effective amount, can be prepared in combination with appropriate pharmaceutical stabilization compounds, delivery vehicles, carriers, inert diluents, and/or other additives appropriate for enteral (oral) administration according to methods well known in the art. The formulation usually provides for release within the stomach or the intestine. The C-tail protein-drug conjugate can be formulated into a liquid, paste, suspension, gel, powder, tablet, capsule, food additive or other standard form. Pharmaceutically compatible binding agents and/or adjuvant materials can be included as part of the composition. Examples include a binder such as microcrystalline cellulose, gum tragacanth, or gelatin; an excipient such as starch or lactose; a disintegrating agent such as alginic acid, Primogen™, or corn starch; a lubricant such as magnesium stearate or sterotes; aglidant such as colloidal silicon dioxide; a sweetening agent such as sucrose or saccharin; and/or a flavoring agent such as peppermint, methyl salicylate, or orange flavoring. When the dosage unit form is a capsule, it can contain, in addition to material of the above type, a liquid carrier. Other dosage unit forms may further include coatings of sugar, shellac, or other enteric agents. The C-tail protein-drug can be administered as a component of a fluid such as an elixir, suspension, beverage, liquid dietary supplement or substitute, or syrup; or of a solid such as a wafer or candy. The C-tail protein-drug can also be mixed with other active materials that do not impair the desired action, or with materials that supplement the desired action.

In one preferred embodiment, C-tail-drug is encapsulated within carriers that effect release in the small intestine, such as microparticles, microcapsules, or microspheres prepared from synthetic or natural polymers such as proteins, polyhydroxy acids, or polysaccharides. Appropriate systems are known to those skilled in the art. Several microsphere formulations have been proposed as a means for oral drug delivery. These formulations generally serve to protect the encapsulated compound and to deliver the compound into the blood stream. Enteric coated formulations have been widely used for many years to protect drugs administered orally, as well as to delay release. Other formulations designed to deliver compounds into the blood stream, as well as to protect the encapsulated drug, are formed of a hydrophobic protein, such as zein, as described in PCT/US90/06430 and PCT/US90/06433; "proteinoids", as described in U.S. Pat. No. 4,976,968 to Steiner; or synthetic polymers, as described in European Patent application 0 333 523 by the UAB Research Foundation and Southern Research Institute. EPA 0 333 523 described microparticles of less than ten microns in diameter that contain antigens, for use in oral administration of vaccines. Larger sizes are preferred for the uses described herein to avoid uptake into the blood and lymph systems of the encapsulated C-tail protein.

The microparticles can be formed of rapidly bioerodible polymers such as poly[lactide-co-glycolide], polyanhydrides, and polyorthoesters, whose carboxylic groups are exposed on the external surface as their smooth surface erodes; natural polymers such as proteins, like zein, modified zein, casein, gelatin, gluten, serum albumin, or collagen, and polysaccharides, like cellulose, dextrans, polyhyaluronic acid, polymers of acrylic and methacrylic esters and alginic acid; synthetic polymers such as polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes and copolymers thereof; and synthetically modified natural polymers such as alkyl celluloses, hydroxyalkyl celluloses, cellulose ethers, cellulose esters, and nitrocelluloses. Representative polymers include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly (ethylene oxide), poly(ethylene terephthalate), poly(vinyl acetate), polyvinyl chloride, polystyrene, polyvinyl pyrrolidone, and polyvinylphenol. Specific representative bioerodible polymers include polylactides, polyglycolides and copolymers thereof, poly(ethylene terephthalate), poly (butyric acid), poly(valeric acid), poly(lactide-co-caprolactone), poly[lactide-co-glycolide], polyanhydrides, polyorthoesters, blends, and copolymers thereof.

These polymers can be obtained from sources such as Sigma Chemical Co., St. Louis, Mo., Polysciences, Warrenton, Pa., Aldrich, Milwaukee, Wis., Fluka, Ronkonkoma, N.Y., and BioRad, Richmond, Calif. or else synthesized from monomers obtained from these suppliers using standard techniques.

Pharmaceutical compositions containing C-tail-drug conjugates must be stable under the conditions of manufacture and storage and may be preserved against contamination by microorganisms, such as bacteria and fungi, through the use of antioxidants such as Vitamin E and ethoxyquin and bacteriostatic agents, which are on the list of compounds approved for use by the Food and Drug Administration.

Modifications and variations of the compositions and methods of use described herein will be obvious to those skilled in the art from the foregoing detailed description. Such modifications and variations are intended to come within the scope of the appended claims.

We claim:

1. A method for delivering a therapeutic composition comprising:
   orally administering to an individual in need thereof a therapeutically effective amount of a C-tail protein conjugated to a therapeutic composition, in combination with a pharmaceutical carrier acceptable for oral administration,
   wherein the C-tail protein comprises at least four eleven amino acid repeats having at least three prolines present in the carboxy terminal region of human bile salt lipase as shown in Sequence ID No. 1 that binds to a specific receptor on intestinal cells.

2. The method of claim 1 wherein the C-tail protein comprises at least four eleven amino acid repeats present in amino acid residues 539 to 722 of Sequence ID No. 1.

3. The method of claim 1 wherein the C-tail protein further comprises the region of bile salt-activated lipase containing the catalytic site which has been inactivated.

4. The method of claim 1 wherein the C-tail protein further comprises at least three of the repeating regions of the primate, human, cat, dog or rodent bile salt-activated lipase.

5. The method of claim 1 wherein the C-tail protein comprises the at least four eleven amino acid proline-rich units.

6. The method of claim 1 wherein the C-tail protein is formed by the substitution of one or more amino acids of Sequence ID No. 1.

7. The method of claim 1 wherein the therapeutic composition is selected from the group consisting of proteins, carbohydrates, nucleic acids, nucleosides, nucleotides, liposomes, inorganic compounds, vitamins, drugs and minerals.

8. The method of claim 1 wherein the therapeutic compound is an enzyme.

9. The method of claim 8 wherein the enzyme catabolizes the compound ingested by the individual.

10. The method of claim 1, wherein the therapeutic composition is a polysaccharide.

11. The method of claim 1, wherein the therapeutic compound is an antigen.

12. The method of claim 1, wherein the therapeutic compound is a procaryotic or eucaryotic cell.

13. The method of claim 1, wherein the therapeutic compound is selected from the group consisting of nonsteroidal anti-inflammatory compounds, anesthetics, chemotherapeutic agents, immunosuppressive agents, steroids, antibiotics, antivirals, antifungals, steroidal anti-inflammatories, and anticoagulants.

14. A composition for delivering a therapeutic composition comprising:
   a therapeutically effective amount of a C-tail protein conjugated to a therapeutic composition, in combination with a pharmaceutical carrier acceptable for oral administration,
   wherein the C-tail protein comprises at least four eleven amino acid repeats having at least three prolines present in the carboxy terminal region of human bile salt lipase as shown in Sequence ID No. 1, that binds to a specific receptor on intestinal cells.

15. The composition of claim 14 wherein the C-tail protein comprises at least four eleven amino acid repeats present in amino acid residues 539 to 722 of Sequence ID No. 1.

16. The composition of claim 1 wherein the C-tail protein further comprises the region of bile salt-activated lipase containing the catalytic site which has been inactivated.

17. The composition of claim 14 wherein the C-tail protein further comprises at least three of the repeating regions of the primate, human, cat, dog or rodent bile salt-activated lipase.

18. The composition of claim 14 wherein the C-tail protein comprises at least ten eleven amino acid proline-rich units.

19. The composition of claim 14 wherein the C-tail protein is formed by the substitution of one or more amino acids of Sequence ID No. 1.

20. The composition of claim 14 wherein the therapeutic composition is selected from the group consisting of proteins, carbohydrates, nucleic acids, nucleosides, nucleotides, liposomes, inorganic compounds, vitamins, drugs and minerals.

21. The composition of claim 14 wherein the therapeutic compound is an enzyme.

22. The composition of claim 21 wherein the enzyme catabolizes the compound ingested by the individual.

23. The composition of claim 14, wherein the therapeutic composition is a polysaccharide.

24. The composition of claim 14, wherein the therapeutic compound is an antigen.

25. The composition of claim 14, wherein the therapeutic compound is a procaryotic or eucaryotic cell.

26. The composition of claim 14, wherein the therapeutic compound is selected from the group consisting of nonsteroidal anti-inflammatory compounds, anesthetics, chemotherapeutic agents, immunosuppressive agents, steroids, antibiotics, antivirals, antifungals, steroidal anti-inflammatories, and anticoagulants.

27. The composition of claim 14 wherein the carrier is a polymer or enteric encapsulating composition and the C-tail protein is incorporated onto or within the carrier.

28. The composition of claim 14 wherein the C-tail protein is in a dietary formulation for oral administration.

29. The composition of claim 14 wherein the C-tail protein is in the milk of a transgenic cow or sheep.

* * * * *